United States Patent
Tanishima et al.

(10) Patent No.: US 9,993,164 B2
(45) Date of Patent: Jun. 12, 2018

(54) MONITORING APPARATUS

(71) Applicants: NIHON KOHDEN CORPORATION, Shinjuku-ku, Tokyo (JP); NATIONAL CEREBRAL AND CARDIOVASCULAR CENTER, Suita-shi, Osaka (JP)

(72) Inventors: Masami Tanishima, Tokyo (JP); Tatsuo Yoshida, Tokyo (JP); Teiji Ukawa, Tokyo (JP); Masafumi Kitakaze, Suita (JP); Osamu Seguchi, Suita (JP)

(73) Assignees: NIHON KOHDEN CORPORATION, Tokyo (JP); NATIONAL CEREBRAL AND CARDIOVASCULAR CENTER, Osaka (JP)

( * ) Notice: Subject to any disclaimer, the term of this patent is extended or adjusted under 35 U.S.C. 154(b) by 0 days. days.

(21) Appl. No.: 14/603,486

(22) Filed: Jan. 23, 2015

(65) Prior Publication Data
US 2015/0208927 A1 Jul. 30, 2015

(30) Foreign Application Priority Data
Jan. 24, 2014 (JP) .................. 2014-011350

(51) Int. Cl.
*A61B 5/0205* (2006.01)
*A61B 5/1455* (2006.01)
(Continued)

(52) U.S. Cl.
CPC .......... *A61B 5/0205* (2013.01); *A61B 5/0836* (2013.01); *A61B 5/14552* (2013.01);
(Continued)

(58) Field of Classification Search
CPC .................................................. A61B 5/0205
See application file for complete search history.

(56) References Cited

U.S. PATENT DOCUMENTS

| 4,368,740 A | * | 1/1983 | Binder | ................. | A61B 5/0836 |
| | | | | | 600/531 |
| 6,428,483 B1 | | 8/2002 | Carlebach | | |

(Continued)

FOREIGN PATENT DOCUMENTS

| JP | 2003-532442 A | 11/2003 |
| JP | 2007-527776 A | 10/2007 |

(Continued)

OTHER PUBLICATIONS

Search Report dated May 27, 2015, issued by the European Patent Office in counterpart European Application No. 15152275.2.
(Continued)

*Primary Examiner* — Carl H Layno
*Assistant Examiner* — Jennifer Ghand
(74) *Attorney, Agent, or Firm* — Sughrue Mion, PLLC

(57) ABSTRACT

A monitoring apparatus includes a condition determining section which is configured to determine a condition of one of a heart, lungs, and blood vessels based on: a concentration of carbon dioxide in an expired gas which is measured by using a first sensor; and an oxygen transport parameter or a metabolic parameter which is measured by using a second sensor.

9 Claims, 11 Drawing Sheets

(51) Int. Cl.
*A61B 5/00* (2006.01)
*A61B 5/083* (2006.01)
*A61B 5/021* (2006.01)
*A61B 5/024* (2006.01)
*A61B 5/01* (2006.01)
*A61B 5/029* (2006.01)
*A61B 5/0402* (2006.01)

(52) U.S. Cl.
CPC ................ *A61B 5/742* (2013.01); *A61B 5/01* (2013.01); *A61B 5/021* (2013.01); *A61B 5/024* (2013.01); *A61B 5/029* (2013.01); *A61B 5/0402* (2013.01)

(56) References Cited

U.S. PATENT DOCUMENTS

| | | | | |
|---|---|---|---|---|
| 8,414,488 | B2* | 4/2013 | Colman | A61B 5/0205 128/200.24 |
| 2002/0082511 | A1 | 6/2002 | Carlebach et al. | |
| 2005/0098527 | A1 | 5/2005 | Yates, III | |
| 2005/0203352 | A1 | 9/2005 | Al-Ali et al. | |
| 2006/0102581 | A1 | 5/2006 | Yates, III | |
| 2006/0108363 | A1 | 5/2006 | Yates, III | |
| 2008/0000866 | A1 | 1/2008 | Yates, III | |
| 2008/0188733 | A1* | 8/2008 | Al-Ali | A61B 5/0205 600/364 |
| 2008/0300471 | A1 | 12/2008 | Al-Ali et al. | |
| 2010/0069725 | A1* | 3/2010 | Al-Ali | A61B 5/0205 600/301 |
| 2010/0317933 | A1 | 12/2010 | Colman et al. | |
| 2010/0317986 | A1 | 12/2010 | Colman et al. | |
| 2011/0040713 | A1 | 2/2011 | Colman et al. | |
| 2011/0098592 | A1 | 4/2011 | Colman et al. | |
| 2012/0022388 | A1 | 1/2012 | Pittman et al. | |
| 2012/0145152 | A1 | 6/2012 | Lain et al. | |
| 2013/0204099 | A1 | 8/2013 | Colman et al. | |
| 2013/0274617 | A1 | 10/2013 | Hosaka et al. | |
| 2013/0289364 | A1 | 10/2013 | Colman et al. | |
| 2014/0012096 | A1* | 1/2014 | Nomura | G06F 19/345 600/301 |
| 2014/0155775 | A1 | 6/2014 | Colman et al. | |
| 2014/0155776 | A1 | 6/2014 | Colman et al. | |
| 2014/0330092 | A1 | 11/2014 | Al-Ali et al. | |
| 2016/0174907 | A1 | 6/2016 | Colman et al. | |
| 2016/0345843 | A1 | 12/2016 | Colman et al. | |

FOREIGN PATENT DOCUMENTS

| | | |
|---|---|---|
| JP | 2011-505177 A | 2/2011 |
| JP | 2012-523262 A | 10/2012 |
| JP | 2013-220175 A | 10/2013 |

OTHER PUBLICATIONS

Communication issued by the Japanese Patent Office dated Aug. 22, 2017, in counterpart Japanese Patent Application No. 2014-011350.
Communication dated Apr. 3, 2018, by the Japanese Patent Office in copending Application No. 2014-011350.

* cited by examiner

FIG. 7

NON-INVASIVE MONITORING OF PULMONARY CONGESTION BY ETCO$_2$, SpO$_2$

| PULMONARY CONGESTION (PULMONARY HYPERTENSION) | PULMO-NARY EDEMA | DEAD ALVEOLI | CONDITION | PATTERN | ARTERIAL BLOOD GAS PaO$_2$ | ARTERIAL BLOOD GAS PaCO$_2$ | NON-INVASIVE MONITORING SpO$_2$ | NON-INVASIVE MONITORING ETCO$_2$ |
|---|---|---|---|---|---|---|---|---|
| NA | NA | NA | NORMAL | A | NORMAL ≈95mmHg | NORMAL ≈40mmHg | NORMAL >96% | NORMAL >36mmHg |
| NA | NA | O | POOR VENTILATION | B | LOW OXYGEN <80mmHg | HIGH CO$_2$ >43mmHg | LOW OXYGEN <95% | HIGH CO$_2$ >40mmHg |
| | O | O | PULMONARY CONGESTION PULMONARY HYPERTENSION (PULMONARY EDEMA) ACUTE EXACERBATION | C | LOW OXYGEN <70mmHg | HIGH CO$_2$ >45mmHg | HIGHLY LOW OXYGEN <90% | SLIGHTLY LOWERED <36mmHg |
| O | NA | NA | PULMONARY CONGESTION PULMONARY HYPERTENSION (NON-PULMONARY EDEMA) CHRONIC/SEVERE | D | SLIGHTLY LOWERED ≈90mmHg | NORMAL ≈40mmHg | SLIGHTLY LOWERED >94% | HIGHLY LOWERED <28mmHg |

MONITORING APPARATUS

CROSS-REFERENCE TO RELATED APPLICATION(S)

This application is based upon and claims the benefit of priority from prior Japanese patent application No. 2014-011350, filed on Jan. 24, 2014, the entire contents of which are incorporated herein by reference.

BACKGROUND

The presently disclosed subject matter relates to a monitoring apparatus for heart failure.

Recently, heart failure becomes one of diseases which frequently occur. In order to prevent heart failure from occurring, for example, it is contemplated to previously determine the possibility of onset of heart failure. JP-T-2012-523262 discloses a method for monitoring pulmonary congestion in a subject based on parameters of the breathing of the subject, in order to previously detect the possibility of onset of heart failure.

In the method for monitoring pulmonary congestion in a subject, which is disclosed in JP-T-2012-523262, however, the possibility of onset of heart failure can be detected, but the specific cause of the onset cannot be determined.

SUMMARY

The presently disclosed subject matter may provide a monitoring apparatus in which the specific cause of onset of heart failure can be determined.

The monitoring apparatus may comprise a condition determining section which is configured to determine a condition of one of a heart, lungs, and blood vessels based on: a concentration of carbon dioxide in an expired gas which is measured by using a first sensor; and an oxygen transport parameter or a metabolic parameter which is measured by using a second sensor.

The first sensor may measure an expired end-tidal carbon dioxide concentration which is a concentration of the carbon dioxide in the expired gas during an end-tidal phase of expiration.

The oxygen transport parameter or the metabolic parameter may include one of an $SpO_2$, blood gas information, a blood pressure, a cardiac output, a cardiac index, a pulsation rate, a body temperature, a pulse rate, and a heart rate.

The cardiac output may be non-invasively measured.

The second sensor may be configured by a pulse wave sensor for measuring a pulse wave, and an electrocardiogram sensor for measuring an electrocardiogram, and non-invasively measure the cardiac output based on the pulse wave and the electrocardiogram.

The condition of one of the heart, the lungs, and the blood vessels which is determined by the condition determining section may be one of heart failure, a ventilation condition, a condition of pulmonary congestion or pulmonary hypertension, and a condition of acute pulmonary congestion or pulmonary hypertension.

The monitoring apparatus may further comprise: a displaying section which is configured to display in a form of a graph the condition of one of the heart, the lungs, and the blood vessels, the condition being classified based on the concentration of the carbon dioxide and the oxygen transport parameter or the metabolic parameter.

A determination reference value for determining the condition of one of the heart, the lungs, and the blood vessels may be indicated in the graph displayed on the displaying section.

BRIEF DESCRIPTION OF THE DRAWINGS

FIG. 7 is a table showing comparisons of measurement data of the patterns shown in FIGS. 2 to 5.

DETAILED DESCRIPTION OF EXEMPLARY EMBODIMENTS

Hereinafter, embodiments of the monitoring apparatus of the presently disclosed subject matter will be described in detail with reference to the drawings.

Figure 1:
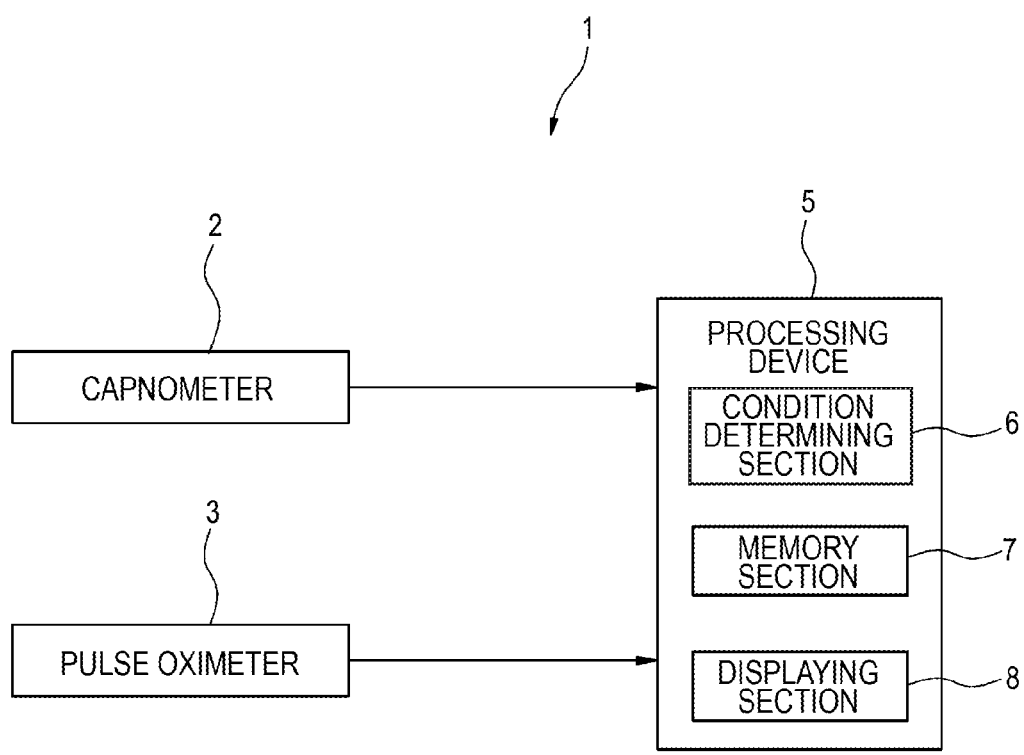
FIG. 1 is a diagram showing an example of the configuration of the monitoring apparatus of the presently disclosed subject matter.

FIG. 1 is a diagram showing the configuration of a monitoring apparatus 1 for monitoring heart failure of the embodiment.

As shown in FIG. 1, the monitoring apparatus 1 includes a processing device 5 which processes biological information measured by a capnometer (an example of the first sensor) 2 for to measuring biological information of the subject, and a pulse oximeter (an example of the second sensor) 3.

The capnometer 2 is a sensor which measures the concentration (%) or partial pressure (mmHg) of carbon dioxide contained in the inspired and expired gases of the subject. When a $CO_2$ sensor or a sampling tube is attached to the nose or mouth of the subject, the capnometer 2 can non-invasively measure the concentration or the like of carbon dioxide contained in the inspired and expired gases. In the embodiment, the capnometer 2 is configured so as to measure the expired end-tidal carbon dioxide partial pressure ($ETCO_2$) exhibiting the concentration of carbon dioxide during the end-tidal phase of expiration in which the concentration in the expired gas is highest. The capnometer 2 is connected to the processing device 5 so that the $ETCO_2$ measured by the capnometer 2 is sent to the processing device 5.

The pulse oximeter 3 is a sensor which measures the pulse rate, the arterial blood oxygen saturation ($SpO_2$), and the like. When a probe is attached to the fingertip or ear of the subject, the pulse oximeter 3 can non-invasively measure the pulse rate and the $SpO_2$. In the embodiment, the pulse oximeter 3 is configured so as to measure the $SpO_2$ which is the oxygen saturation of the arterial blood. The pulse oximeter 3 is connected to the processing device 5 so that the $SpO_2$ measured by the pulse oximeter 3 is sent to the processing device 5. The second sensor is not limited to the pulse oximeter, and any sensor may be used as far as the sensor can measure an oxygen transport parameter or a metabolic parameter. The oxygen transport parameter or the metabolic parameter may be the $SpO_2$, blood gas information, the blood pressure, the cardiac output, the cardiac index, the pulsation rate, the body temperature, the pulse rate, the heart rate, or the like. As the second sensor, for example, a pulse wave sensor for measuring the pulse wave, and an electrocardiogram sensor for measuring an electrocardiogram are useful. Based on the pulse wave and electrocardiogram which are measured by a pulse wave sensor and an electrocardiogram sensor, the cardiac output can be non-invasively measured.

The processing device 5 includes a condition determining section 6, a memory section 7, and a displaying section 8.

The condition determining section 6 determines the conditions of the heart, the lungs, and blood vessels of the subject based on the $ETCO_2$ measured by using the capnometer 2, and the $SpO_2$ measured by using the pulse oximeter 3. On the basis of the determined condition of the respiratory system, the condition determining section 6 classifies decreases which cause heart failure, and determines the condition (severity). As described above, the condition determining section 6 can determine the condition of one of the heart, the lungs, and blood vessels based on the measurement result of the $ETCO_2$ and the oxygen transport parameter or the metabolic parameter. The conditions of the heart, the lungs, and blood vessels include heart failure, the ventilation condition, the condition of pulmonary congestion or pulmonary hypertension, and the condition of acute pulmonary congestion or pulmonary hypertension, or the like.

The memory section 7 stores biological information including the $ETCO_2$ and $SpO_2$ which are measured by the capnometer 2 and the pulse oximeter 3, and data such as thresholds which function as a comparison reference for determining the conditions of the heart, the lungs, and blood vessels.

The displaying section 8 includes a display screen. The displaying section 8 plots and displays biological information including the $ETCO_2$ and $SpO_2$ which are measured by the capnometer 2 and the pulse oximeter 3, on two-dimensional coordinates displayed on the display screen. The displaying section 8 displays the determination result (the condition (decease) of the respiratory system and the severity) of the condition determining section 6. The displaying section 8 may display the comparison reference for determining the conditions of the heart, the lungs, and blood vessels.

Next, a method of classifying decreases which cause heart failure will be described.

Depending on the ventilation and the blood flow, for example, the condition of the respiratory system can be classified into Patterns A to D such as shown in FIGS. 2 to 5. Patterns A to D diagrammatically show manners of gas exchange performed in the lungs, respectively. In FIGS. 2 to 5, the identical or similar portions are denoted by the same reference numerals.

Figure 2:
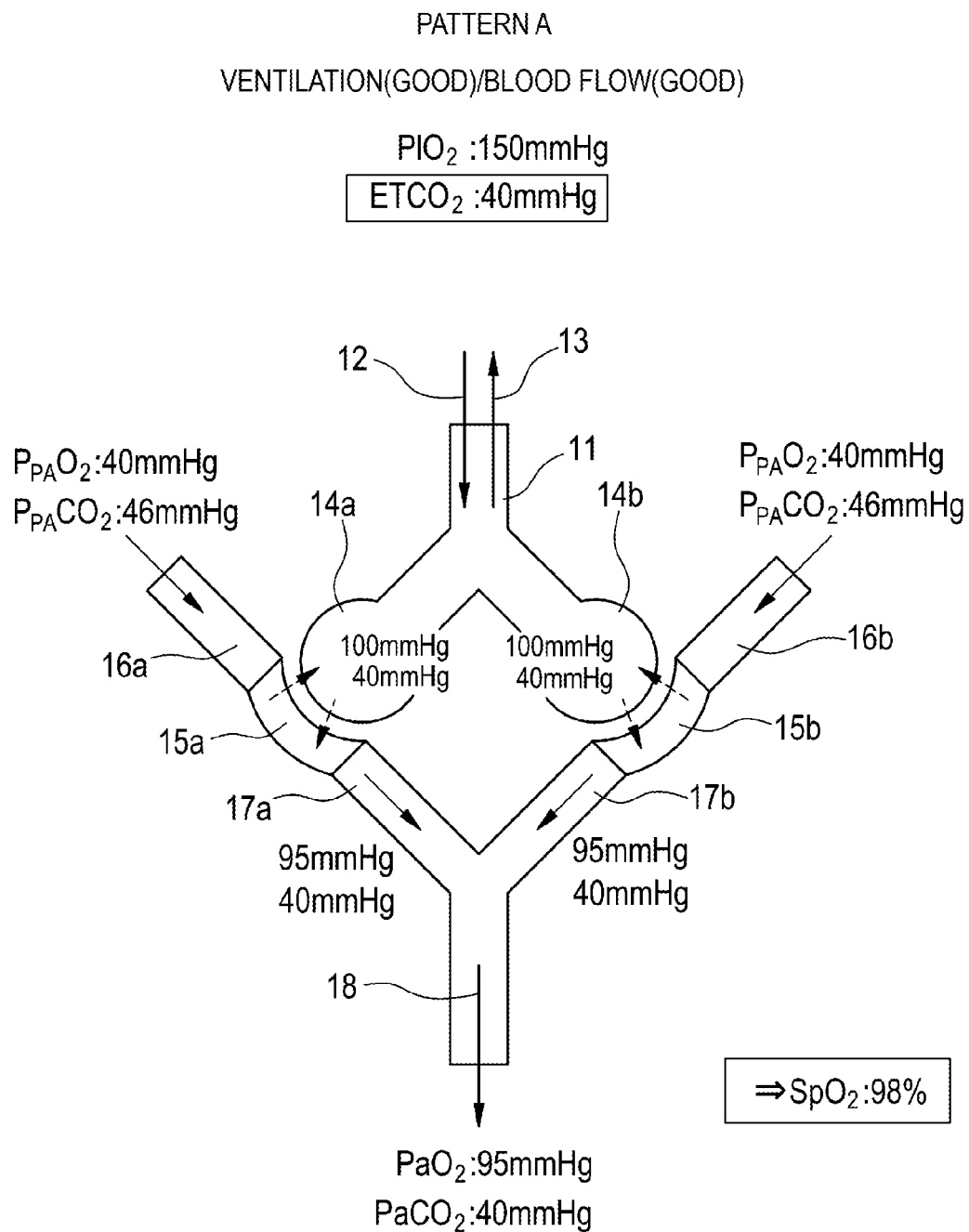
FIG. 2 is a diagram showing an example of patterns of the ventilation and blood flow in a respiratory system.

Pattern A shown in FIG. 2 indicates values of oxygen and carbon dioxide that are measured from various portions of a subject having a normal respiratory system in which the ventilation and the blood flow are satisfactorily performed.

In FIG. 2, $PIO_2$ indicates the inspired oxygen partial pressure which is the partial pressure of oxygen contained in the inspired gas during inspiration. "$PIO_2$: 150 mmHg" means that the inspired oxygen partial pressure in one respiration is 150 mmHg. $ETCO_2$ indicates the expired end-tidal carbon dioxide partial pressure which is the partial pressure of carbon dioxide during the end-tidal phase of expiration that is contained in the expired gas during expiration. "$ETCO_2$: 40 mmHg" means that the expired end-tidal carbon dioxide partial pressure in one respiration is 40 mmHg.

Moreover, $P_{PA}O_2$ indicates the partial pressure of oxygen in pulmonary arterial blood which is the partial pressure of oxygen contained in the blood from the vena cava. "$P_{PA}O_2$: 40 mmHg" means that the partial pressure of oxygen in pulmonary arterial blood is 40 mmHg. $P_{PA}CO_2$ indicates the partial pressure of carbon dioxide in pulmonary arterial blood which is the partial pressure of carbon dioxide contained in the blood from the vena cava. "$P_{PA}CO_2$: 46 mmHg" means that the partial pressure of carbon dioxide in pulmonary arterial blood is 46 mmHg.

Oxygen ($PIO_2$: 150 mmHg) sucked from the nose and mouth of the subject is introduced into the lungs through the airway 11 as indicated by the arrow 12. Carbon dioxide ($ETCO_2$: 40 mmHg) which has undergone gas exchange in the lungs is discharged from the nose and the mouth through the airway 11 to the outside of the body as indicated by the arrow 13.

Gas exchange in which oxygen is introduced and carbon dioxide is discharged is performed between alveoli 14a, 14b and pulmonary capillaries 15a, 15b which surround the alveoli.

Part of $PIO_2$: 150 mmHg is lost until oxygen reaches the alveoli 14a, 14b, and the partial pressure is lowered. As a result, the alveolar oxygen partial pressure which is the partial pressure of oxygen in the alveoli is 100 mmHg.

The blood ($P_{PA}O_2$: 40 mmHg, $P_{PA}CO_2$: 46 mmHg) from the vena cava (not shown) is sent to the pulmonary capillaries 15a, 15b via the heart (not shown) through the pulmonary arteries 16a, 16b.

In gas exchange, the blood in the pulmonary capillaries 15a, 15b introduces oxygen from the air in the alveoli 14a, 14b, and pushes out carbon dioxide in the blood into the alveoli 14a, 14b. When oxygen is introduced from the alveoli 14a, 14b, the partial pressure of oxygen in the blood is raised from 40 mmHg to 95 mmHg. When carbon dioxide is pushed out from the blood, the partial pressure of carbon dioxide in the blood is lowered from 46 mmHg to 40 mmHg. The blood which has undergone gas exchange in the alveoli 14a, 14b in the pulmonary capillaries 15a, 15b is sent to the pulmonary veins 17a, 17b. The blood in the pulmonary veins 17a, 17b flows as indicated by the arrow 18 to be sent to the aorta (not shown) via the heart.

In FIG. 2, $PaO_2$ indicates the arterial blood oxygen partial pressure which is the partial pressure of oxygen contained in the arterial blood. "$PaO_2$: 95 mmHg" means that the arterial blood oxygen partial pressure is 95 mmHg. Moreover, $PaCO_2$ indicates the arterial blood carbon dioxide partial pressure which is the partial pressure of carbon dioxide contained in the arterial blood. "$PaCO_2$: 40 mmHg" means that the arterial blood carbon dioxide partial pressure is 40 mmHg.

Figure 6:
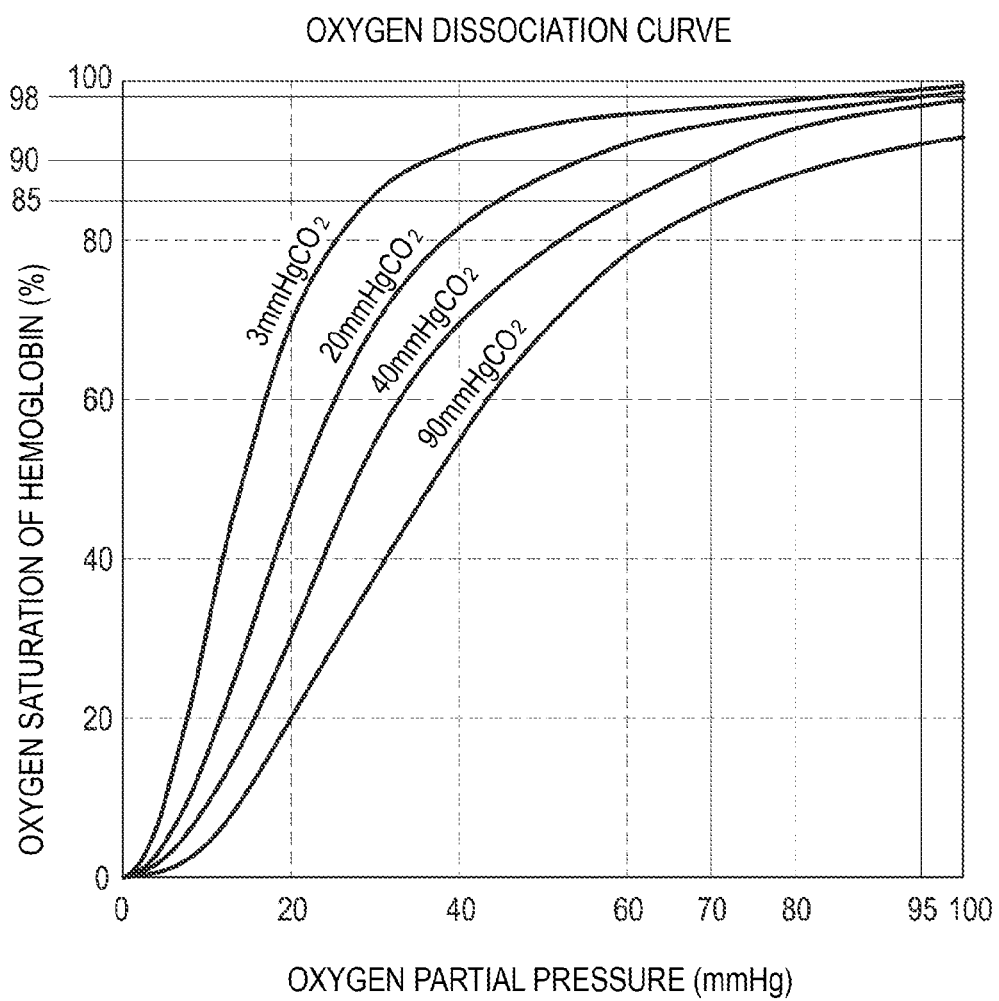
FIG. 6 is a view showing an oxygen dissociation curve of hemoglobin.

Furthermore, "$SpO_2$: 98%" means that the arterial blood oxygen saturation is 98%. This value is obtained from the oxygen dissociation curve shown in FIG. 6 which will be described later. The oxygen dissociation curve shows relationships between the oxygen partial pressure and the oxygen saturation of hemoglobin. In the case where the arterial blood oxygen partial pressure (PaO$_2$) is 95 mmHg as in Pattern A of FIG. 2, the SpO$_2$ is 98%.

As shown in FIG. 2, the same value of 40 mmHg is measured as the ETCO$_2$ and the PaCO$_2$. In the case of a normal subject, in this way, the ETCO$_2$ and the PaCO$_2$ have the same or similar values.

Figure 3:
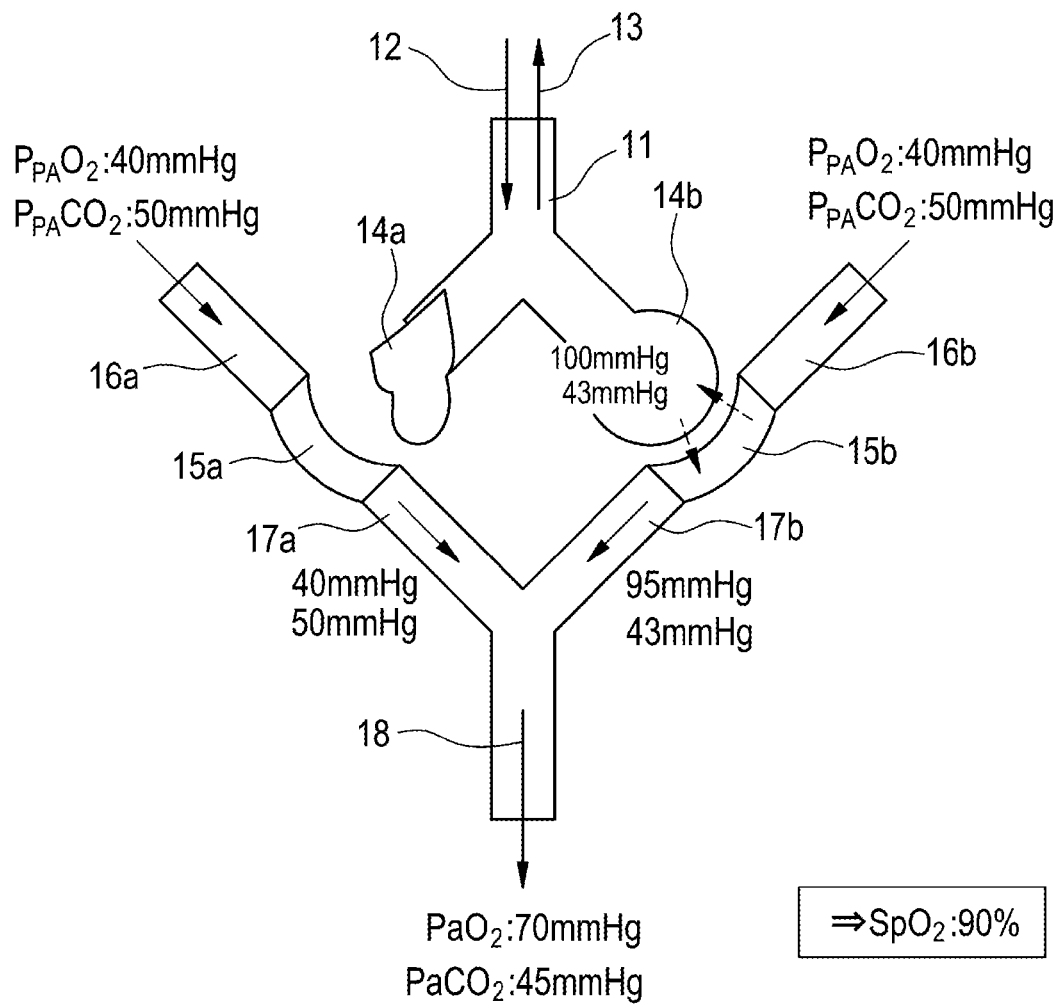
FIG. 3 is a diagram showing an example of patterns of the ventilation and blood flow in a respiratory system.

Pattern B shown in FIG. 3 indicates values of oxygen and carbon dioxide that are measured from various portions of a subject having a respiratory system in which the blood flow is satisfactory, but the ventilation is not satisfactorily performed or the ventilation is poor. Pattern B shows the case where a poor ventilation is caused by collapse of the alveoli 14a.

Since the alveoli 14a are collapsed, the oxygen does not reach the alveoli 14a. Therefore, gas exchange is performed only between the normal alveoli 14b and the pulmonary capillaries 15b, and is not performed between the collapsed alveoli 14a and the pulmonary capillaries 15a. Therefore, the blood flown from the pulmonary artery 16a does not undergo gas exchange in the lung, and flows out as it is from the pulmonary vein 17a, and the oxygen partial pressure of 40 mmHg and carbon dioxide partial pressure of 50 mmHg in the blood remain as they are.

The blood (oxygen partial pressure: 40 mmHg, carbon dioxide partial pressure: 50 mmHg) in the pulmonary vein 17a is mixed with the blood (oxygen partial pressure: 95 mmHg, carbon dioxide partial pressure: 43 mmHg) in the pulmonary vein 17b, and then flows as indicated by the arrow 18 to be sent to the aorta via the heart. In the arterial blood, as result, the PaO$_2$ is 70 mmHg, and the PaCO$_2$ is 45 mmHg. The value of the SpO$_2$ with respect to PaO$_2$: 70 mmHg is SpO$_2$: 90% from the oxygen dissociation curve of FIG. 6.

The carbon dioxide which is discharged to the outside of the body through the airway 11 consists of only the carbon dioxide that has undergone gas exchange in the normal alveoli 14b, and carbon dioxide is not discharged from the collapsed alveoli 14a. As a result, the ETCO$_2$ discharged to the outside of the body is 43 mmHg. In the case of Pattern B, as described above, the value (45 mmHg) of the PaCO$_2$ is measured as a value which is slightly higher than the value (43 mmHg) of the ETCO$_2$.

Figure 4:
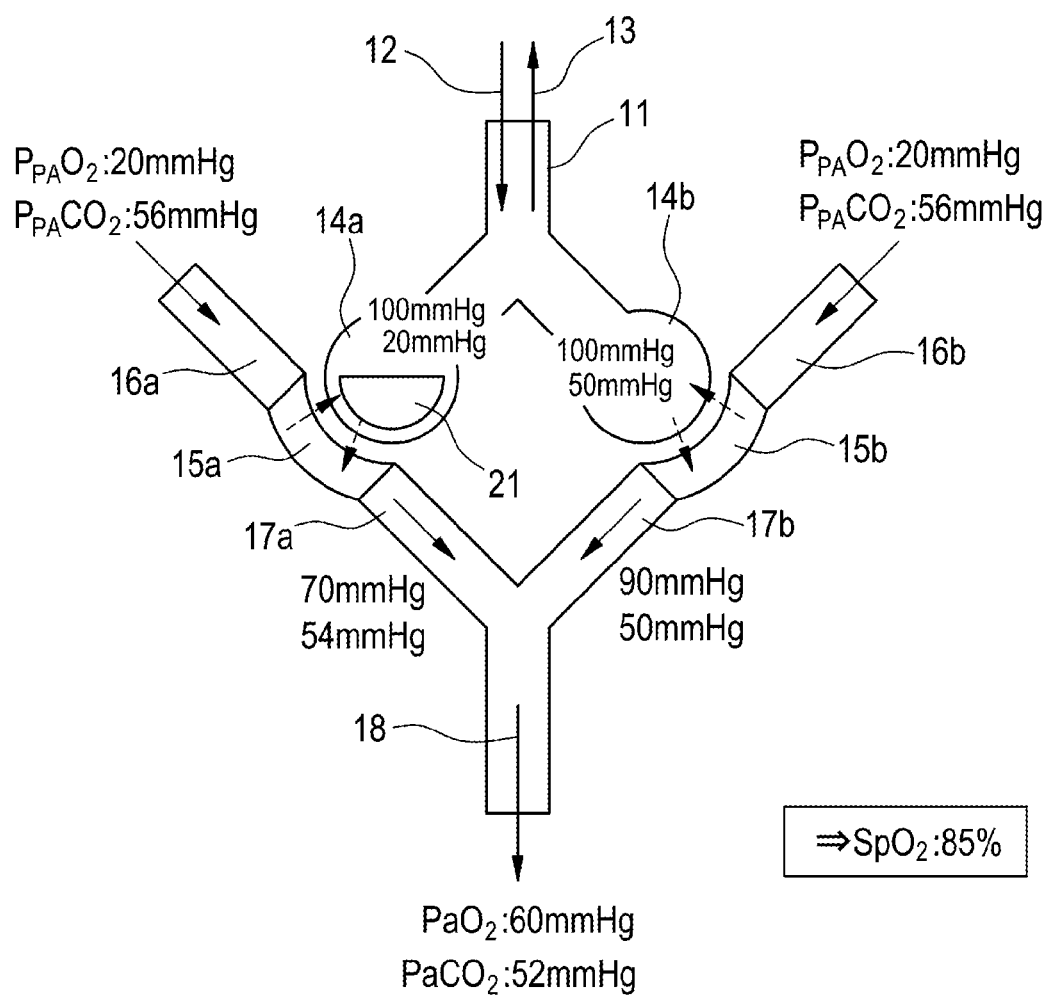
FIG. 4 is a diagram showing an example of patterns of the ventilation and blood flow in a respiratory system.

Pattern C shown in FIG. 4 indicates values of oxygen and carbon dioxide that are measured from various portions of a subject having a respiratory system in which, similarly with Pattern B, the blood flow is satisfactory, but the ventilation is poor. Pattern C shows the case where a poor ventilation is caused by pulmonary edema.

The pressure of the pulmonary capillaries 15a is raised, water in blood leaks into the alveoli 14a, and water 21 stays in the alveoli 14a. Therefore, impaired diffusion occurs between the alveoli 14a and the pulmonary capillaries 15a, and the efficiency of gas exchange between the alveoli 14a and the pulmonary capillaries 15a is lowered. Gas exchange between the alveoli 14b and the pulmonary capillaries 15b is normally performed.

Due to the water 21 in the alveoli 14a, the blood in the pulmonary capillaries 15a hardly introduces oxygen from the alveoli 14a. Therefore, the oxygen partial pressure (20 mmHg) of the blood in the pulmonary artery 16a is raised only to 70 mmHg in the pulmonary vein 17a. Due to the water 21 in the alveoli 14a, moreover, the blood in the pulmonary capillaries 15a hardly pushes out carbon dioxide into the alveoli 14a. Therefore, the carbon dioxide partial pressure (56 mmHg) of the blood in the pulmonary artery 16a is lowered only to 54 mmHg also in the pulmonary vein 17a. The value of the $P_{P4}O_2$ is lowered to 20 mmHg by the reduction of the arterial blood oxygen partial pressure (PaO$_2$).

The blood (oxygen partial pressure: 70 mmHg, carbon dioxide partial pressure: 54 mmHg) in the pulmonary vein 17a is mixed with the blood (oxygen partial pressure: 90 mmHg, carbon dioxide partial pressure: 50 mmHg) in the pulmonary vein 17b, and then flows as indicated by the arrow 18 to be sent to the aorta via the heart. In the arterial blood, as result, the PaO$_2$ is 60 mmHg, and the PaCO$_2$ is 52 mmHg. The value of the SpO$_2$ with respect to PaO$_2$: 60 mmHg is SpO$_2$: 85% from the oxygen dissociation curve of FIG. 6.

The carbon dioxide which is discharged to the outside of the body through the airway 11 consists of the carbon dioxide that has undergone gas exchange in the alveoli 14a in which impaired diffusion occurs, and the carbon dioxide that has undergone gas exchange in the normal alveoli 14b. Therefore, 20 mmHg which is the carbon dioxide partial pressure in the alveoli 14a, and 50 mmHg which is the carbon dioxide partial pressure in the alveoli 14b are mixed with each other, and the ETCO$_2$ which is discharged to the outside of the body is 30 mmHg. In the case of Pattern C, in this way, the value (30 mmHg) of the ETCO$_2$ is measured as a value which is lower than the value (52 mmHg) of the PaCO$_2$.

Figure 5:
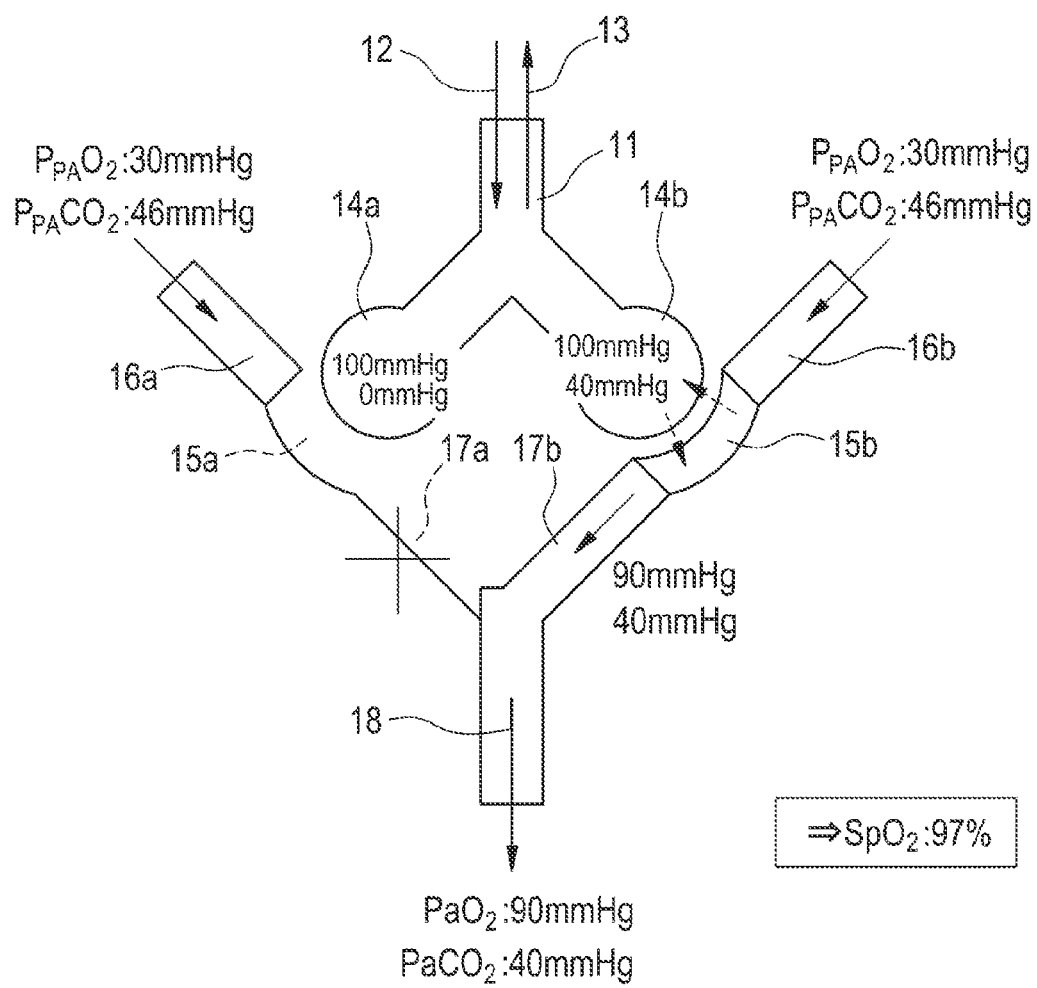
FIG. 5 is a diagram showing an example of patterns of the ventilation and blood flow in a respiratory system.

Pattern D shown in FIG. 5 indicates values of oxygen and carbon dioxide that are measured from various portions of a subject having a respiratory system in which the ventilation is satisfactory, but the blood flow is poor. Pattern D shows the case where constriction occurs in peripheral blood vessels of the pulmonary artery 16a and the blood flow is poor.

The blood in the pulmonary artery 16a does not flow into the pulmonary capillaries 15a and the pulmonary vein 17a because of the constriction in peripheral blood vessels. Therefore, gas exchange between the alveoli 14a and the pulmonary capillaries 15a is not performed. Since gas exchange is not performed, the carbon dioxide partial pressure in the alveoli 14a is equal to that in the inspired gas or 0 mmHg.

By contrast, normal gas exchange is performed between the alveoli 14b and the pulmonary capillaries 15b. Therefore, the oxygen partial pressure which is 30 mmHg in the blood in the pulmonary artery 16b is raised to 90 mmHg in the blood in the pulmonary vein 17b, and the carbon dioxide partial pressure which is 46 mmHg in the blood in the pulmonary artery 16b is lowered to 40 mmHg in the blood in the pulmonary vein 17b. As a result of gas exchange, the carbon dioxide partial pressure in the alveoli 14b is 40 mmHg. The value of the $P_{P4}O_2$ is lowered to 30 mmHg by an influence of the reduction of the carbon dioxide partial pressure.

Since the blood flow does not exist in the pulmonary vein 17a, the blood (oxygen partial pressure: 90 mmHg, carbon dioxide partial pressure: 40 mmHg) in the pulmonary vein 17b flows as indicated by the arrow 18 to be sent to the aorta via the heart. In the arterial blood, as result, the PaO$_2$ is 90 mmHg, and the PaCO$_2$ is 40 mmHg. The value of the SpO$_2$ with respect to PaO$_2$: 90 mmHg is SpO$_2$: 97% from the oxygen dissociation curve of FIG. 6.

The carbon dioxide which is discharged to the outside of the body through the airway 11 consists of the carbon dioxide in the alveoli 14a where gas exchange is not performed, and that in the alveoli 14b where normal gas exchange is performed. Therefore, 50 mmHg which is the carbon dioxide partial pressure in the alveoli 14a, and 40 mmHg which is the carbon dioxide partial pressure in the alveoli 14b are mixed with each other, and the $ETCO_2$ which is discharged to the outside of the body is 20 mmHg. In the case of Pattern D, in this way, the value (20 mmHg) of the $ETCO_2$ is measured as a value which is largely lower than the value (40 mmHg) of the $PaCO_2$.

FIG. 7 showing comparisons of data measured from sets of a plurality of subjects. The sets correspond to Patterns A to D of FIGS. 2 to 5, respectively.

In FIG. 7, the contents of the items shown in the first row indicate the contents measured from subjects having a normal respiratory system corresponding to Pattern A of FIG. 2.

Since the respiratory system is in the normal condition, the subjects do not fall under any of pulmonary congestion (pulmonary hypertension), pulmonary edema, and dead alveoli (NA: Not Applicable). In the arterial blood, the value of the $PaO_2$ was about 95 mmHg, and that of the $PaCO_2$ was about 40 mmHg. The value (98% in the example of FIG. 2) of the $SpO_2$ which can be non-invasively monitored was larger than 96%, and the value (40 mmHg in the example of FIG. 2) of the $ETCO_2$ was larger than 36 mmHg.

In FIG. 7, the contents of the items shown in the second row indicate the contents measured from subjects having a respiratory system in which the ventilation is poor because of, for example, collapse of alveoli, corresponding to Pattern B of FIG. 3.

Because of the poor ventilation caused by collapse of alveoli, the subjects do not fall under pulmonary congestion (pulmonary hypertension) and pulmonary edema, and fall under dead alveoli (symbol of ○). In the arterial blood, the value (70 mmHg in the example of FIG. 3) of the $PaO_2$ was smaller than 80 mmHg, and the value of the $PaCO_2$ was about 45 mmHg. As compared with Pattern A, a tendency of low oxygen and high carbon dioxide was shown. The value (90% in the example of FIG. 3) of the $SpO_2$ which can be non-invasively monitored was smaller than 95%, and the value (43 mmHg in the example of FIG. 3) of the $ETCO_2$ was larger than 40 mmHg. As compared with Pattern A, a tendency of low oxygen and high carbon dioxide was shown.

In FIG. 7, the contents of the items shown in the third row indicate the contents measured from subjects having a respiratory system in which the ventilation is poor because of pulmonary edema, corresponding to Pattern C of FIG. 4.

It is supposed that, because of the poor ventilation caused by pulmonary edema, the blood volume in blood vessels was increased, the pressure in pulmonary capillaries was raised, and water in blood oozed out into alveoli. Therefore, the subjects can fall under any of pulmonary congestion (pulmonary hypertension), pulmonary edema, and dead alveoli (symbol of ○). Pulmonary edema has characteristics that the severities of pulmonary congestion and pulmonary hypertension are acutely impaired. In the arterial blood, the value (60 mmHg in the example of FIG. 4) of the $PaO_2$ was smaller than 70 mmHg, and the value of the $PaCO_2$ was about 52 mmHg. As compared with Pattern A, a tendency of high carbon dioxide and low oxygen was shown. The value (85% in the example of FIG. 4) of the $SpO_2$ which can be non-invasively monitored was smaller than 90%, and the value (30 mmHg in the example of FIG. 4) of the $ETCO_2$ was smaller than 36 mmHg. As compared with Pattern A, a tendency of low oxygen and low carbon dioxide was shown.

In FIG. 7, the contents of the items shown in the fourth row indicate the contents measured from subjects having a respiratory system in which the blood flow is poor because of, for example, constriction of pulmonary blood vessels, corresponding to Pattern D of FIG. 5.

Because of poor blood flow caused by constriction of pulmonary blood vessels, the subjects fall under pulmonary congestion (pulmonary hypertension), but do not fall under pulmonary edema and dead alveoli. Poor blood flow caused by constriction of pulmonary blood vessels has characteristics that chronic pulmonary congestion and pulmonary hypertension become severe. In the arterial blood, the value of the $PaO_2$ was about 90 mmHg, the value of the $PaCO_2$ was about 40 mmHg, oxygen was slightly low, and carbon dioxide was normal. The value (97% in the example of FIG. 5) of the $SpO_2$ which can be non-invasively monitored was larger than 94%, and the value (20 mmHg in the example of FIG. 5) of the $ETCO_2$ was smaller than 28 mmHg. As compared with Pattern A, a tendency in which oxygen is slightly lower, and carbon dioxide is largely lowered was shown.

Figure 8:
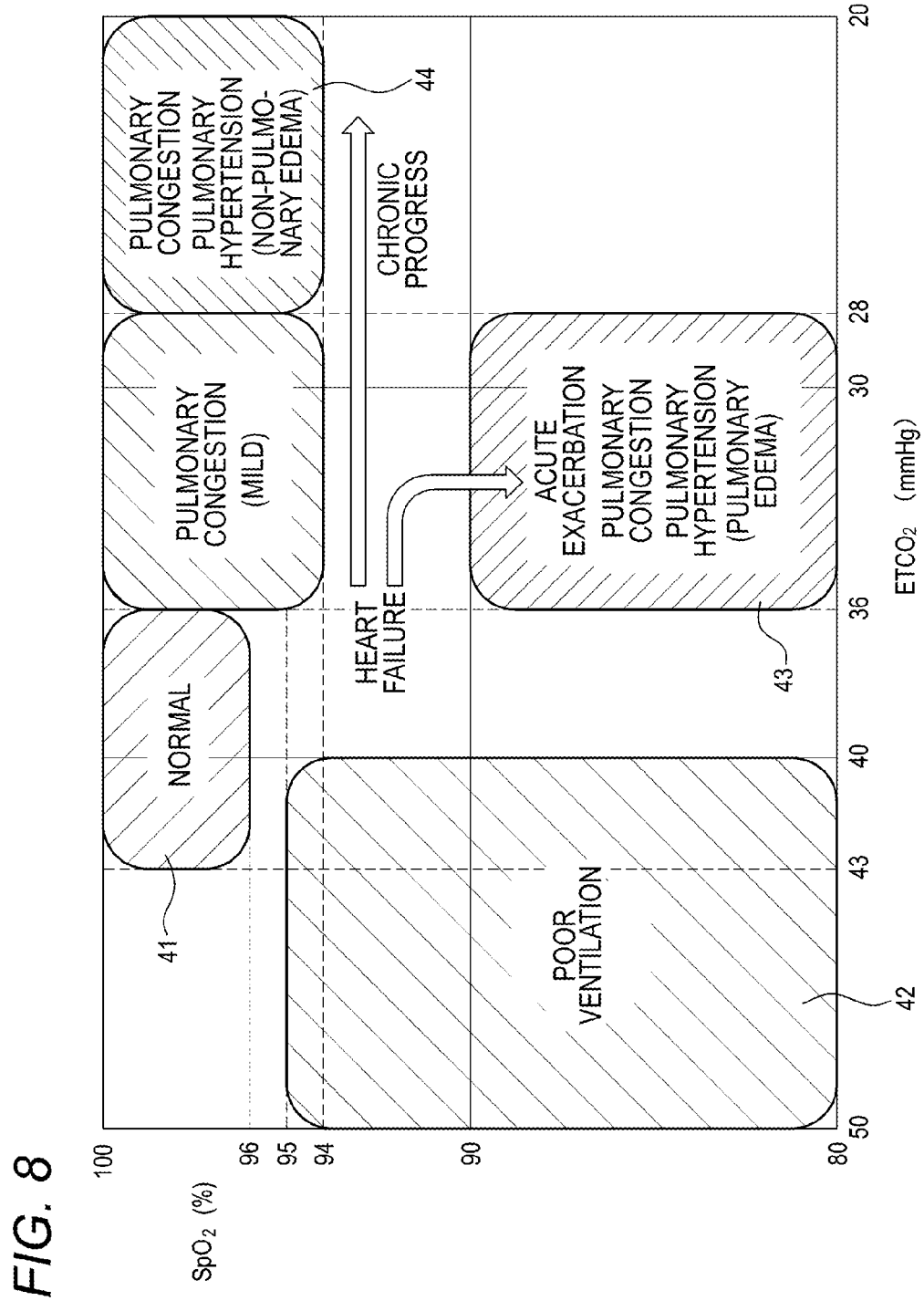
FIG. 8 is a view showing classifications of conditions of decreases which cause heart failure, according to the $ETCO_2$ and the $SpO_2$.

FIG. 8 shows a state where conditions of decreases which can be classified by the $ETCO_2$ and the $SpO_2$, and which cause heart failure are displayed in the form of a graph on the displaying section 8. The conditions of the decreases which are shown in FIG. 8 are classified based on non-invasively monitored values of the $ETCO_2$ and the $SpO_2$ which are shown in FIG. 7. Although not explicitly shown in FIG. 8, the measurement results are chronologically plotted in the graph. The form of a graph may be a form in which one of the $ETCO_2$ and the $SpO_2$ is indicated on the ordinate, and the other is indicated on the abscissa, and not limited to the display form shown in FIG. 8.

For example, the case where the measured value of the $ETCO_2$ is larger than 36 mmHg, and the value of the $SpO_2$ is larger than 96% is classified into the condition 41 of "Condition of respiratory system is normal."

For example, the case where the measured value of the $ETCO_2$ is larger than 40 mmHg, and the value of the $SpO_2$ is smaller than 95% is classified into the condition 42 of "Respiratory system is in condition where ventilation is poor."

For example, the case where the measured value of the $ETCO_2$ is smaller than 36 mmHg, and the value of the $SpO_2$ is smaller than 90% is classified into the condition 43 of "Respiratory system is in condition of pulmonary edema."

For example, the case where the measured value of the $ETCO_2$ is smaller than 28 mmHg, and the value of the $SpO_2$ is larger than 94% is classified into the condition 44 of "Respiratory system is in condition of pulmonary congestion or pulmonary hypertension which is chronic and highly severe."

The condition of one of the heart, the lungs, and blood vessels which is classified based on the $ETCO_2$ and the oxygen transport parameter or the metabolic parameter (for example, the $SpO_2$, blood gas information, the blood pressure, the cardiac output, the cardiac index, the pulsation rate, the body temperature, the pulse rate, and the heart rate) may be displayed in the form of a graph on the displaying section 8. The blood gas information may be measurement items of a blood gas test of the arterial blood oxygen partial pressure ($PaO_2$), the arterial blood carbon dioxide partial pressure ($PaCO_2$), the pH, the Hb, the Hct, and the like.

Next, the operation of the monitoring apparatus 1 will be described.

The value of the $ETCO_2$ which is measured by using the capnometer 2, and that of the $SpO_2$ which is measured by using the pulse oximeter 3 are input to the processing device 5. The condition determining section 6 of the processing device 5 compares the input values of the $ETCO_2$ and the $SpO_2$ with the thresholds which are previously set. The thresholds which function as a comparison reference are previously stored in the memory section 7.

Here, the thresholds which function as a comparison reference mean the values of the $ETCO_2$ and the $SpO_2$ which function to as a comparison reference for classifying conditions of the respiratory system that have been described with reference to FIG. 8. For example, values such as $SpO_2$: 90%, $ETCO_2$: 36 mmHg, and $ETCO_2$: 28 mmHg correspond to thresholds which function as a comparison reference.

In a manner similar to that of the classification which has been described with reference to FIG. 8, based on the result of the comparison, the condition determining section 6 determines which one of the normal condition, the condition where the ventilation is poor, the condition of chronic pulmonary congestion or pulmonary hypertension, and the condition of pulmonary edema due to acute pulmonary congestion or pulmonary hypertension corresponds to the condition of the respiratory system of the subject. The result of the determination is stored together with the measurement data of the $ETCO_2$ and the $SpO_2$ in the memory section 7.

On the two-dimensional coordinates displayed on the display screen of the displaying section 8, the section plots biological information A including the measurement data of the $ETCO_2$ measured by the capnometer 2 and those of the $SpO_2$ measured by the pulse oximeter 3. The displaying section 8 further displays the determination result (the condition (decease) of the respiratory system and the severity) of the condition determining section 6. The displaying section 8 may display the comparison reference on the two-dimensional coordinates to displayed on the display screen of the section, as regions defined by the thresholds of the $SpO_2$ and the $ETCO_2$ as shown in FIG. 8. Namely, the displaying section 8 may display the regions corresponding to the above-described conditions 41 to 44.

According to the above-described monitoring apparatus 1 of the embodiment, the values of the $ETCO_2$ and the $SpO_2$ are measured from the subject, whereby the condition of the respiratory system which causes heart failure can be determined more finely. Therefore, for example, it is possible to determine the condition where both the ventilation and the blood flow are satisfactorily performed, that where the ventilation is poor because of collapse of the alveoli 14a, that where the ventilation is poor because of pulmonary edema due to acute severity of pulmonary congestion or pulmonary hypertension, and that where the blood flow is poor because of chronic severity of pulmonary congestion or pulmonary hypertension. According to the embodiment, therefore, it is possible to determine one of the conditions of the heart, the lungs, and blood vessels which cause onset of heart failure.

Moreover, the displaying section 8 plots and displays the measurement data of the $ETCO_2$ and those of the $SpO_2$ on the two-dimensional coordinates, and therefore the medical person can visually evaluate the conditions of the heart, the lungs, and blood vessels. Furthermore, the medical person can know rapidly and easily a change of the condition of heart failure by observing the locus of the plots (the locus of time series data of the biological information A) and regions (comparison reference) corresponding to the conditions 41 to 44 which are displayed on the displaying section 8.

When the medical person evaluates in combination the measurement data of the $ETCO_2$ and those of the $SpO_2$, the conditions of the heart, the lungs, and blood vessels can be quantitatively evaluated. Therefore, also when these values of an unconscious subject are measured, for example, the degree of progress of the disease can be determined, and hence an adequate procedure can be rapidly applied to the subject.

The $ETCO_2$ can be measured by using the capnometer 2, and the $SpO_2$ can be measured by using the pulse oximeter. Therefore, the $ETCO_2$ and the $SpO_2$ can be simply measured by using non-invasive devices, and the monitoring apparatus 1 can be easily used in home medicine.

Figure 9:
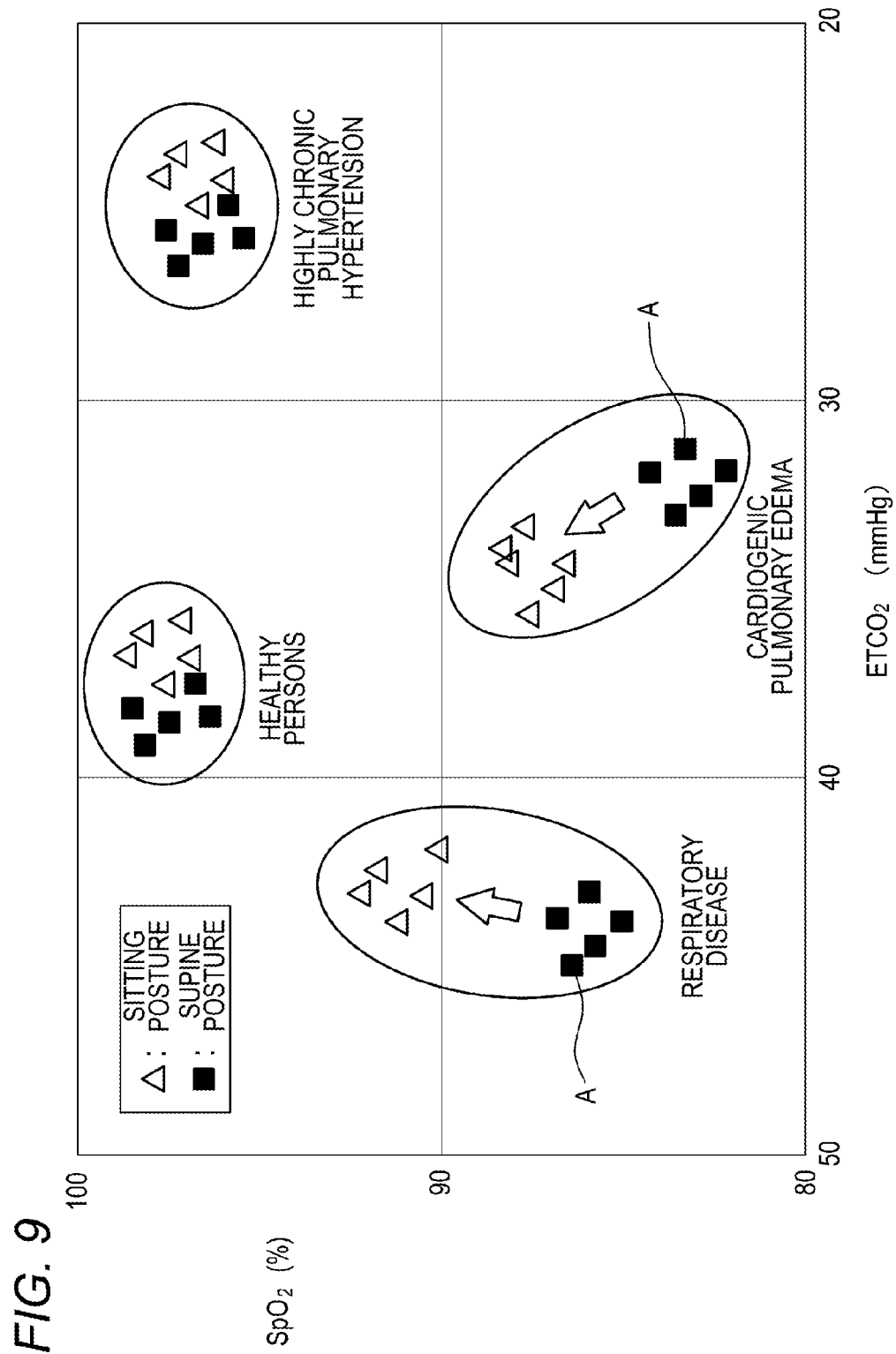
FIG. 9 is a view for diagnosing the severity of pulmonary edema based on the $ETCO_2$ and the $SpO_2$.

Next, a data change which is due to the posture of the subject, and which is measured by the monitoring apparatus 1 will be described with reference to FIG. 9.

The subject changed the posture from a supine posture in which the subject lay on the back on a bed, to a sitting posture in which the subject on the bed raised only the upper body, and data of the $ETCO_2$ and the $SpO_2$ were measured from the subject. FIG. 9 shows an example of results of the measurement.

The values of the $ETCO_2$ and the $SpO_2$ were measured by using the capnometer 2 and the pulse oximeter 3. The plurality of plot points (■: supine posture, Δ: sitting posture) indicated in FIG. 9 show measurement data of the $ETCO_2$ and the $SpO_2$ which were measured from subjects in the respective posture. It was noted that, in the case of healthy persons and highly chronic pulmonary hypertension, the values of the $ETCO_2$ and the $SpO_2$ which were measured in supine and sitting postures are substantially unchanged as shown in FIG. 9.

Moreover, the subjects were asked about a change of the degree of pain which was felt when the posture was changed from a supine posture to a sitting posture. As a result, it was noted that, as shown in FIG. 9, in the case where a subject suffers from pulmonary edema, in accordance with a posture change from a supine posture to a sitting posture, biological information A (■: supine posture) including the measurement data of the $ETCO_2$ and the $SpO_2$ transits from a coordinate position indicating the category of "condition of pulmonary edema due to acute pulmonary congestion or pulmonary hypertension" exemplified in FIG. 8, to that indicating "normal condition" on the two-dimensional coordinates displayed on the display screen of the displaying section 8. Moreover, it was noted that, in the case where the severity of pulmonary edema of a subject is high, this tendency appears notably as compared with the case where the severity is low. It is considered that these phenomena are caused by the fact that, in a sitting posture, the ratio of alveoli in which water stays is reduced as compared with the case of a supine posture, and the influence of water is suppressed. It was further noted that, also in the case where a subject suffers from respiratory disease, biological information A transits to the normal condition. This phenomenon is caused by the fact that the functional residual capacity (FRC) is increased in the case of a sitting posture.

As described above, when the $ETCO_2$ and the $SpO_2$ are measured and evaluated in combination, it is possible to quantitatively determine the existence or non-existence and severity of pulmonary edema. Also when these values are measured from an unconscious subject, for example, the existence or non-existence and degree of progress of pulmonary edema can be determined, and hence an adequate procedure can be rapidly applied to the subject. Moreover, this method can detect onset of pulmonary edema caused by an excess of transfusion, and can be applied also to non-invasive monitoring of transfusion management.

Next, a modification (monitoring apparatus 50) of the monitoring apparatus 1 will be described with reference to FIGS. 10 and 11. The components having the same configuration as those of the monitoring apparatus 1 shown in FIG. 1 are denoted by the identical reference numerals, and their description is omitted.

Figure 10:
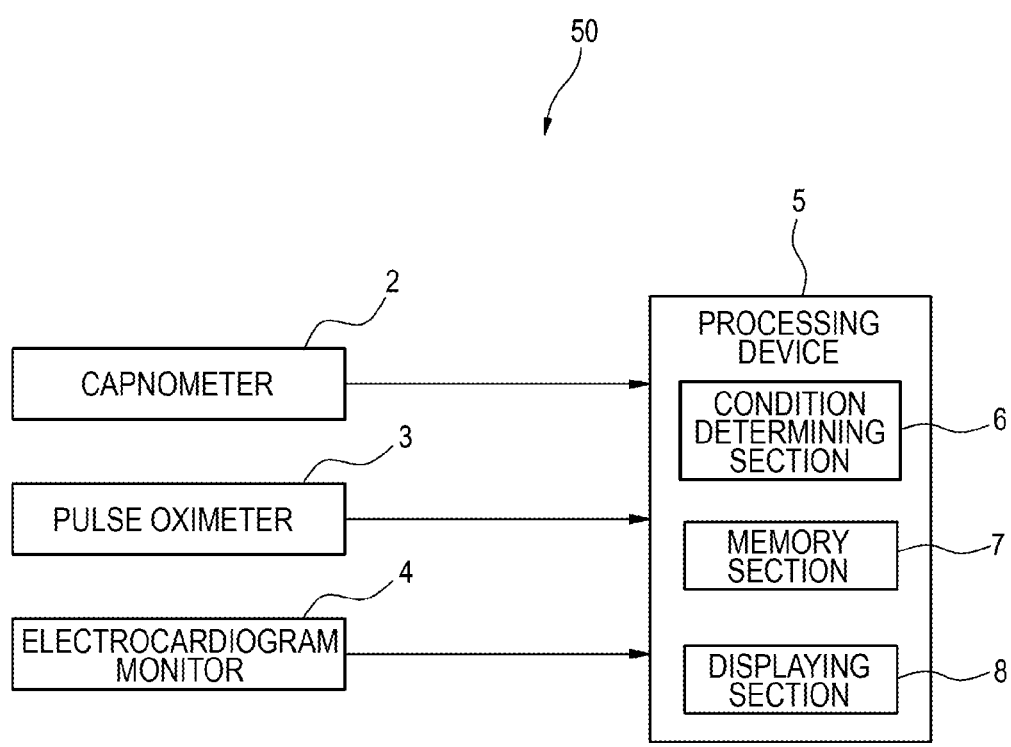
FIG. 10 is a diagram showing a modification example of the configuration of the monitoring apparatus of the presently disclosed subject matter.

FIG. 10 shows the configuration of the monitoring apparatus 50. As shown in FIG. 10, the monitoring apparatus 50 is different from the monitoring apparatus 1 in that the apparatus 50 includes an electrocardiogram monitor 4. The monitoring apparatus 50 can diagnose the severities of pulmonary congestion and pulmonary hypertension.

Figure 11:
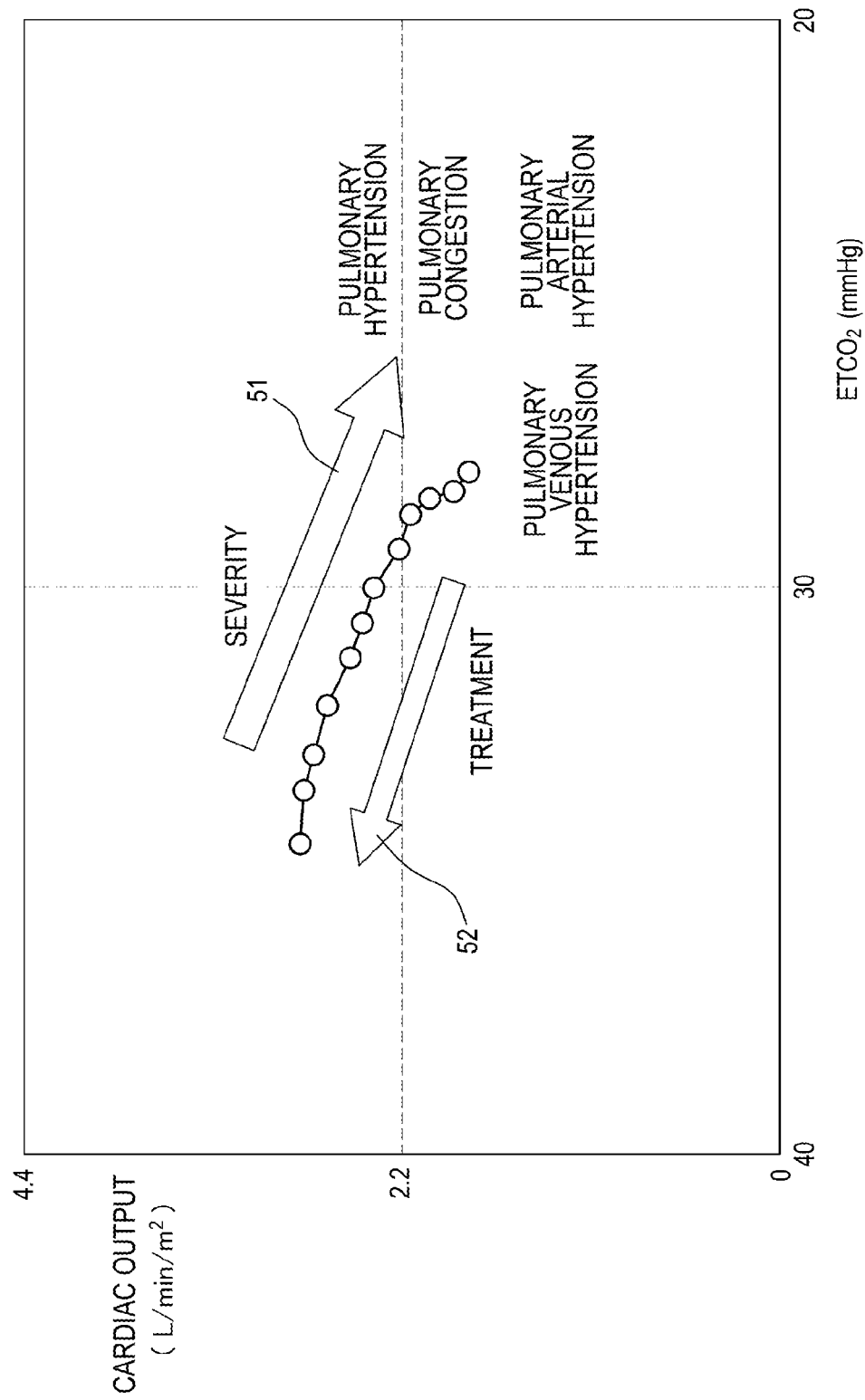
FIG. 11 is a view for diagnosing the severities of pulmonary congestion and pulmonary hypertension based on the $ETCO_2$ and the cardiac output.

FIG. 11 is a view for diagnosing the severities of pulmonary congestion and pulmonary hypertension based on the values of the $ETCO_2$ and cardiac output which are measured from the subject.

The severities of pulmonary congestion and pulmonary hypertension are diagnosed by the monitoring apparatus 50 in the following manner.

The $SpO_2$ and the pulse wave are measured by using the pulse oximeter 3, and the electrocardiogram waveform is measured by using the electrocardiogram monitor 4. The cardiac output is calculated based on the electrocardiogram waveform and the pulse wave propagation time of the pulse wave. For example, the method of calculating the cardiac output is similar to that disclosed in JP-A-2005-312947 which has been filed by the assignee of the present application.

The values of the $ETCO_2$ and the cardiac output are measured from a plurality of subjects suffering from pulmonary congestion or pulmonary hypertension. The measurement from each subject is continuously performed during a period from a time when symptoms get worse, to that when the disease is cured. The measured values are stored as comparison reference data in the memory section 7.

The plurality of plot points (each is indicated by a symbol of ◯) shown in FIG. 11 indicate an example of a graph of the values of the $ETCO_2$ and cardiac output which are continuously measured from subjects suffering from pulmonary congestion or pulmonary hypertension. As shown in FIG. 11, when the severity becomes higher, the measured values of both the $ETCO_2$ and the cardiac output are further reduced, and the plot points of the measured values are further moved in the direction of the arrow 51. By contrast, in accordance with when the disease is further cured by treatment, the measured values of both the $ETCO_2$ and the cardiac output are more increased, and the plot points of the measured values are more moved in the direction of the arrow 52.

The measured data are input to the processing device 5, and formed as a graph similarly with FIG. 11. When measured data of the $ETCO_2$ and the cardiac output are formed as a graph and compared as described above, the severities of pulmonary congestion and pulmonary hypertension can be diagnosed by a classification equivalent to the Forrester classification which is non-invasive and continuous.

The invention is not limited to the above-described embodiment and modification, and may be adequately subjected to modifications, improvements, and the like. In addition, the materials, shapes, dimensions, values, forms, numbers, places, and the like of the components of the above-described embodiment are arbitrary and not limited insofar as the invention is achieved.

According to the monitoring apparatus of the presently disclosed subject matter, it is possible to determine one of the conditions of the heart, the lungs, and blood vessels which cause onset of heart failure.

What is claimed is:
1. A monitoring apparatus comprising:
a condition determining section which is configured to determine a condition of one of a heart, lungs, and blood vessels based on: a concentration of carbon dioxide in an expired gas which is measured by using a first sensor and an oxygen transport parameter or a metabolic parameter which is measured by using a second sensor;
a displaying section which is configured to display in a form of a graph the condition of one of the heart, the lungs, and the blood vessels, the condition being classified based on the concentration of the carbon dioxide and the oxygen transport parameter or the metabolic parameter, wherein the displaying section displays the concentration of the carbon dioxide and the oxygen transport parameter or the metabolic parameter, on two-dimensional coordinates from an origin, the oxygen transport parameter or the metabolic parameter being indicated on an ordinate from the origin, and the concentration of the carbon dioxide being indicated on an abscissa from the origin, the concentration of the carbon dioxide parameter on the abscissa decreasing from a high value at the origin to lower values that are lower than the high value along the abscissa; and
a memory configured to store in association: concentrations of carbon dioxide in an expired gas, oxygen transport parameters or metabolic parameters, and one of a condition of heart failure, a ventilation condition, a condition of pulmonary congestion or pulmonary hypertension, and a condition of acute pulmonary congestion or pulmonary hypertension that is indicated by the concentrations of carbon dioxide in the expired gas and oxygen transport parameters or metabolic parameters,
wherein the condition determining section comprises a processor configured to:
compare the concentration of carbon dioxide in an expired gas which is measured by using the first sensor and the oxygen transport parameter or a metabolic parameter which is measured by using the second sensor with the concentrations of carbon dioxide in the expired gas and oxygen transport parameters or metabolic parameters stored in the memory,
determine the one of the condition of heart failure, the ventilation condition, the condition of pulmonary congestion or pulmonary hypertension, and the condition of acute pulmonary congestion or pulmonary hypertension that is indicated by the concentrations of carbon dioxide in the expired gas and oxygen transport parameters or metabolic parameters in the memory that matches the concentration of carbon dioxide in the expired gas which is measured by using the first sensor and the oxygen transport parameter or a metabolic parameter which is measured by using the second sensor, and
control the displaying section to display in a form of a graph the concentration of the carbon dioxide which is measured by using the first sensor and the oxygen transport parameter or the metabolic parameter which is measured by using the second sensor, and to display, on the graph, regions indicating the one of the condition of heart failure, the ventilation condition, the condition of pulmonary congestion or pulmonary hypertension, and the condition of acute pulmonary congestion or pulmonary hypertension that is indicated by the concentrations of carbon dioxide in the expired gas and oxygen transport parameters or metabolic parameters in the memory.

2. The monitoring apparatus according to claim 1, wherein the first sensor measures an expired end-tidal carbon dioxide concentration which is a concentration of the carbon dioxide in the expired gas during an end-tidal phase of expiration.

3. The monitoring apparatus according to claim 1, wherein the oxygen transport parameter or the metabolic parameter includes one of an arterial blood oxygen saturation ($SpO_2$), blood gas information, a blood pressure, a cardiac output, a cardiac index, a pulsation rate, a body temperature, a pulse rate, and a heart rate.

4. The monitoring apparatus according to claim 3, wherein the cardiac output is non-invasively measured.

5. The monitoring apparatus according to claim 4, wherein the second sensor is configured by a pulse wave sensor for measuring a pulse wave, and an electrocardiogram sensor for measuring an electrocardiogram, and non-invasively measures the cardiac output based on the pulse wave and the electrocardiogram.

6. The monitoring apparatus according to claim 1, wherein a determination reference value for determining the condition of one of the heart, the lungs, and the blood vessels is indicated in the graph displayed on the displaying section.

7. The monitoring apparatus according to claim 1, wherein the regions are defined by thresholds of the concentrations of carbon dioxide in an expired gas and the oxygen transport parameters or metabolic parameters that indicate one of the condition of heart failure, the ventilation condition, the condition of pulmonary congestion or pulmonary hypertension, and the condition of acute pulmonary congestion or pulmonary hypertension.

8. The monitoring apparatus according to claim 7, wherein the thresholds are previously set in the memory.

9. The monitoring apparatus according to claim 8, wherein the thresholds are set in the memory by a medical personnel.

* * * * *